(12) United States Patent
Myrick et al.

(10) Patent No.: US 6,198,531 B1
(45) Date of Patent: Mar. 6, 2001

(54) OPTICAL COMPUTATIONAL SYSTEM

(75) Inventors: Michael L. Myrick; Matthew P. Nelson, both of Columbia, SC (US); Karl S. Booksh, Tempe, AZ (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 08/891,577

(22) Filed: Jul. 11, 1997

(51) Int. Cl.$^7$ ........................................ G01D 3/00
(52) U.S. Cl. ................... 356/300; 356/323; 356/213; 356/222
(58) Field of Search ..................... 356/213, 222, 356/360, 323

(56) References Cited

U.S. PATENT DOCUMENTS

| | | | |
|---|---|---|---|
| 4,084,880 | 4/1978 | Clow | 350/3.72 |
| 4,118,106 | 10/1978 | Leith | 350/96.25 |
| 4,687,335 | 8/1987 | Zupanick et al. | 356/416 |
| 4,934,782 | 6/1990 | Soffer et al. | 350/162.12 |
| 5,005,946 | 4/1991 | Brandstetter | 350/162.12 |
| 5,289,289 | 2/1994 | Nagasaki . | |
| 5,321,539 | 6/1994 | Hirabayashi et al. | 359/94 |
| 5,412,465 | 5/1995 | Baylor et al. | 356/301 |
| 5,459,677 | 10/1995 | Kowalski et al. | 364/571.02 |
| 5,479,164 | 12/1995 | Yorks et al. . | |
| 5,513,022 | 4/1996 | Son et al. | 359/16 |
| 5,555,128 | 9/1996 | Khoury et al. | 359/559 |
| 5,737,076 | 4/1998 | Glaus et al. . | |
| 5,828,492 | 10/1998 | Moser et al. | 359/575 |

FOREIGN PATENT DOCUMENTS

0600334A2   6/1994   (EP) .

OTHER PUBLICATIONS

Photographs of Buhler system.
Applied Optics, Implementation of a Numerical Needle Method For Thin–Film Design, vol. 35, No. 28, pp. 5484–5492, Oct. 1, 1996.
Applied Optics, Refinement of Optical Multilayer Systems With Different Optimization Procedures, vol. 29, pp. 2876–2893, Jul. 1, 1990.
International Search Report, Jan. 19, 1999.
A.G. Ryabenko and G.G. Kasparov, "An Algorithm for Constructing the Basis of Optimal Linear Combinations. Spectral Determination of Aerosol Impurities against the background of a Water Aerosol with an Arbitrary Particle Size Distribution," *Pattern Recognition and Image Analysis*, vol. 3; No. 1, Mar. 1993, pp. 348–354.
A.G. Ryabenko and G.G. Kasparov, "Numerical Study of a Pattern Recognition Multispectral System with Optimal Spectral Splitting," *Pattern Recognition and Image Analysis*, vol. 1; No. 3, 1991, pp. 57–68.
Vasil'ev, et al, "Rotational and Vibrational Deactivation of Excited HF Molecules," *Sov. Physics—JETP*, vol. 41; No. 4, 1976, pp. 617–621.
Moravskii, et al., "Spectrophotometric Determination of the Yield of the $C_{60}$ and $C_{70}$ Fullerenes in Electric Arc Synthesis under Helium," *Journal of Analytical Chemistry*, vol. 53; No. 12, 1998, pp. 1135–1142.

*Primary Examiner*—Frank G. Font
*Assistant Examiner*—Reginald A. Ratliff
(74) *Attorney, Agent, or Firm*—Nelson, Mullins, Riley & Scarborough, LLP

(57) ABSTRACT

An optical analysis system includes an optical filter mechanism disposed to receive light from a light source and configured to optically compress data carried by the light into at least one orthogonal component of the light. A detector mechanism in operative communication with the optical filter mechanism measures a property of the at least one orthogonal component to measure the data.

57 Claims, 7 Drawing Sheets

OPTICAL COMPUTATIONAL SYSTEM

BACKGROUND OF THE INVENTION

The present invention relates to spectroscopy analysis systems. More particularly, the invention relates to improvements in the compression of data carried by light so that information about the light may be obtained.

Light conveys information through data. When light interacts with matter, for example, it carries away information about the physical and chemical properties of the matter. A property of the light, for example its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{(Equation 1)}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique which takes m spectra with n independent variables and constructs a new set of eigenvectors that are linear combinations of the original variables. The eigenvectors may be considered a new set of plotting axes. The primary axis, termed the first principal component, is the vector which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n^{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \qquad \text{(Equation 2)},$$

where y is octane rating, $a_n$ are constants determined by the regression analysis, and $x_1$, $x_2$, $x_3$ and x4 are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \qquad \text{(Equation 3)},$$

where y is octane rating, $a_0$ is the first regression constant from Equation 2, $b_n$ is the sum of the multiple of each regression constant an from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

An example of a conventional spectroscopy analysis system is provided in FIG. 4. A laser 20 directs light to a sample 22 by a bandpass filter 24, beam splitter 26, lens 28 and fiber optic cable 30. Light is reflected back through cable 30 through beam splitter 26 to a lens 32 to a spectrograph 34. Spectrograph 34 separates light from the illuminated sample by wavelength so that the intensity of the light at each wavelength can be measured by a detection device including a charge couple detector 36. Charge couple detector 36 is controlled by controller 38 and cooled by cooler 40. The detection device measures the light intensity of light from spectrograph 34 at each wavelength and outputs this data digitally to a computer 42, which stores the light intensity over the wavelength range. Computer 42 also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. A typical instrument including such sensitive detectors, and the spectrographs needed for their operation, generally cost around $250,000. Furthermore, the devices are sensitive to environmental conditions. In a refinery, for example, they must be protected from explosion, vibration and temperature fluctuations and are often placed in protective housings approximately the size of a refrigerator. The total cost for these instruments may range from $200,000 to $500,000. The power requirements, cooling requirements, cost, complexity and maintenance requirements of these systems have made them impractical in many applications.

SUMMARY OF THE INVENTION

The present invention recognizes and addresses the foregoing disadvantages, and others, of prior art construction and methods.

Accordingly, it is an object of the present invention to provide an improved system for deriving information from light.

It is a further object of the present invention to employ an optical filter mechanism to optically compress data carried by light into orthogonal components.

It is a still further object of the present invention to optically compress data carried by light into components of the light so that data carried by said light may be measured by measuring a property of the components.

Some of these objects are achieved by an optical analysis system. The system comprises an optical filter mechanism disposed to receive light from a light source and configured to optically compress data carried by the light into at least one orthogonal component of the light. A detector mechanism is in operative communication with the optical filter mechanism to measure a property of the at least one orthogonal component to measure the data.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
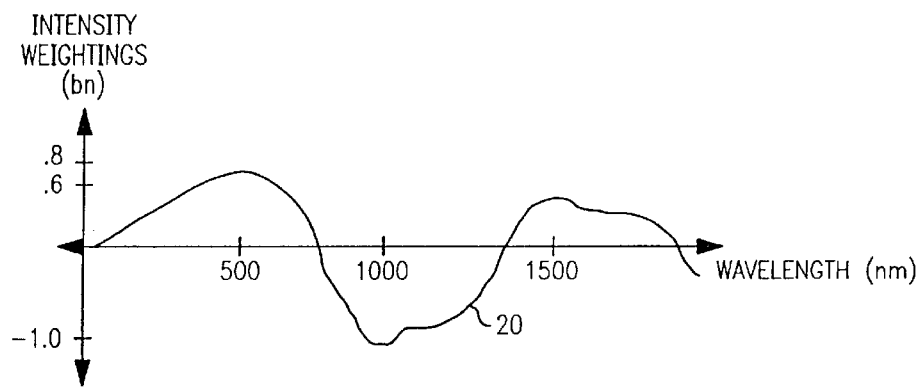
FIG. 1 is a graphical representation of an exemplary spectroscopic regression vector.
Figure 2:
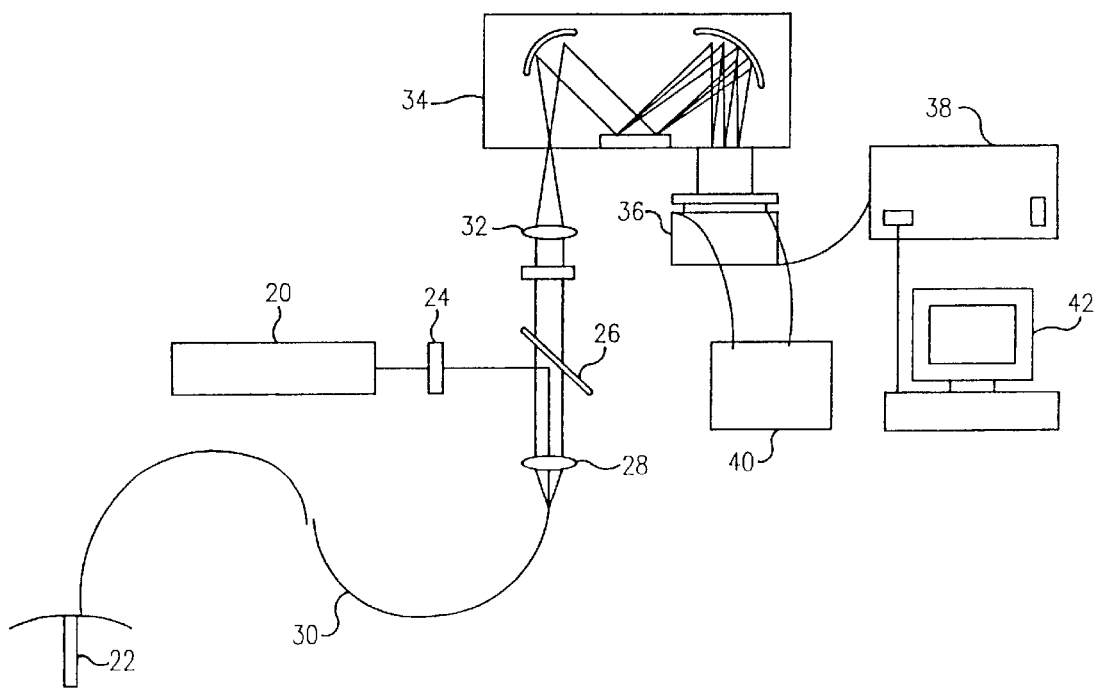
FIG. 2 is a schematic representation of a prior art spectroscopy analysis system.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

Figure 3A:
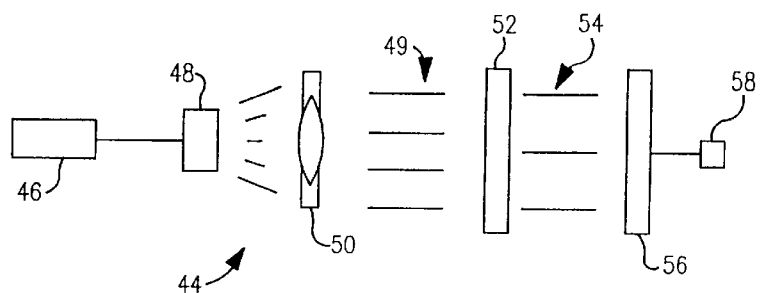
FIG. 3A is a schematic illustration of an optical analysis system according to the present invention.

In one presently preferred embodiment of an optical analysis system, shown generally at 44 in FIG. 3A, an energy source 46 illuminates a sample substance 48. Light passing through or reflected from sample 48 is collimated by collimator 50, which includes one or more lenses or mirrors to focus light from sample 48 into a parallel beam 49. Light from collimator 50 is conveyed, for example through air, fiber optic cable, or other suitable medium, to optical filter 52. Optical filter 52 is an interference device. That is, its performance depends upon the path that light takes through it. Thus, collimator 50 directs a parallel beam 49 to the filter. Light may be directed through a bandpass filter prior to optical filter 52 to eliminate light at wavelengths other than those encompassed by the regression vector.

Collimator 50 is not a spectrograph. Thus, the light in light beam 49 is unseparated, multiple wavelength light. Filter 52, however, is a wavelength-specific light intensity filter. That is, the weighting it applies to the light varies by wavelength. For example, suppose a light beam includes light at two wavelengths, 500 nm and 1000 nm, and that the light intensity at 500 nm is G and the light intensity at 1000 nm is H. The total light intensity is G+H. A filter such as filter 52 may be configured to simultaneously filter the 500 nm light by 50% and the 1000 nm light by 75%, even though the light at the two wavelengths are combined parts of the same light beam. Accordingly, a light intensity detector measuring the output of the filter would measure an intensity of 0.5 G+0.75 H.

In one preferred embodiment, an optical filter 52 includes multiple layers of materials having different refractive indices. By properly selecting the materials and designing the layer spacings, the filter can be made to selectively pass predetermined fractions of light at different wavelengths. Once the desired weighting at each wavelength is determined, the materials and spacings that compose optical filter 52 may be determined using a variety of approximation methods. These methods include, for example, determining the inverse Fourier transform (IFT) of the optical transmission spectrum and structuring the filter as the physical representation of the IFT. The IFT suggests a continuous variation of the refractive index within the filter structure. At present, however, Applicants are unaware of a process for producing such a continuously varying filter, and, therefore, further approximations are used to convert the IFT into a usable structure based on known materials with constant refractive indices. Such filters may be obtained through the research group including George Dobrolski and Pierre Verly under the National Research Council of Canada. Information regarding the structure of such filters is provided at Applied Optics, Vol. 35, pp. 5484–5492 (1996) and Vol. 29, pp. 2876–2893 (1990).

In another preferred embodiment, a direct iterative process known as the "needle" method is used to construct the filter. This method begins with the refractive indices of know$_n$ materials and an estimate of the filter thickness. Through a computer algorithm, the effect of inserting "needles" of a second material into a first material is estimated. These needles are then moved around within the second material, using the interference pattern they create as a guide, until a best approximation of the desired interference pattern is produced. It should be understood that other suitable iterative methods may be used to produce the filter.

In one preferred embodiment of the present invention, the weightings that filter 52 applies at each wavelength are set to the regression weightings $b_n$ described with respect to Equation 3 in the Background of the Invention. Thus, optical filter 52 optically performs the dot product of light beam 49 and a desired regression vector, and the intensity of light 54 output from optical filter 52 is directly related to the desired information. For example, if sample 48 is a gasoline sample, and if the regression vector embodied by filter 52 is an octane regression vector for that particular gasoline type, the intensity of light 54 is directly related to the octane of sample 48.

Accordingly, filter 52 simultaneously and optically perform two spectroscopic analysis steps. First, it compresses data carried by light 49 into orthogonal components. Second, it weights the orthogonal component magnitudes by regression vector weightings so that the output of the filter is directly related to desired information.

Although, as discussed in more detail below, various types of orthogonal components may be used, the orthogonal components in the octane example may be assumed to be principal components since the light characteristics of the light source, the illuminated gasoline sample 48, are known. Since gasoline samples 48 measured by system 44 are similar, the regression constants $a_n$ as in Equation 2 may be calculated and combined to determine regression constants $b_n$ as in Equation 3. Thus, optical filter 52 performs the dot product of the light 49 and the regression vector.

A detector 56 receives weighted light 54 from filter 52 and measures its intensity. The measured intensity is the sum of the intensity at each wavelength of light 54. As noted above, the intensity of light 54 is directly related to the actual measurement of the information associated with the regression vector. If the regression vector includes an offset value $a_0$ as in Equation 3, this may be introduced by a processor 58 which receives the output from detector 56. The processor may also scale the output, to account for normalization of the orthogonal components used to derive the regression vector as described above, so that the final output reflects an actual measurement of the desired information. The scaling may also be performed by one or more amplifiers following the detector, by an optical filter between filter 52 and detector 56, or by filter 52 if the scaling factor is incorporated into the wavelength weightings. Processor 58 may be a stand-alone device or may be incorporated by the detector. It may comprise a microprocessor, for example in a stand-alone computer, or digital and/or analog circuitry. It may also include a display meter to display the detector output in a modified or unmodified form and/or an output device so that the detector output may be directed to external systems for processing. Where there is no offset $a_0$, or where all scaling is to be performed by an external system, the processor 58 may consist solely of a display meter and/or output device.

As noted above, detector 56 may be a conventional light detector, for example constructed from germanium or silicon, for measuring the intensity of incident light. It should be understood, however, that any other suitable light detector devices may be used, for example including cameras or other film devices.

Figure 3B:
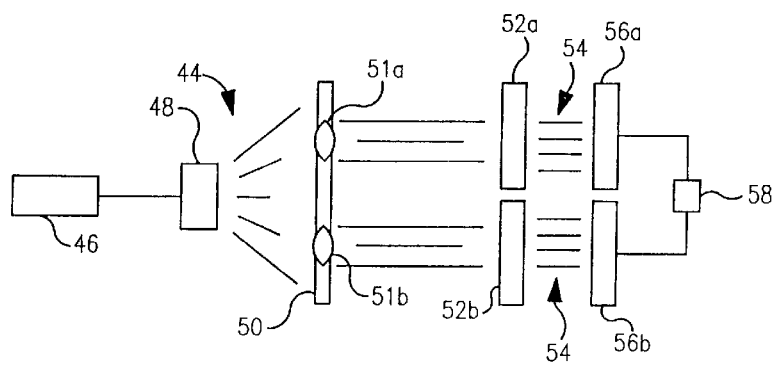
FIG. 3B is a schematic illustration of an optical analysis system according to the present invention.
Figure 3C:
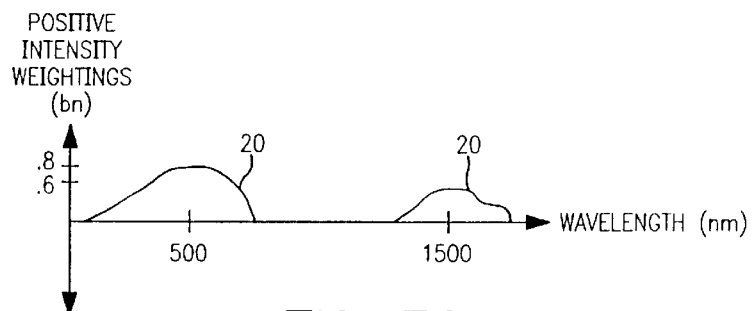
FIG. 3C is a graphical representation of the positive component of the spectroscopic regression vector as in FIG. 1.
Figure 3D:
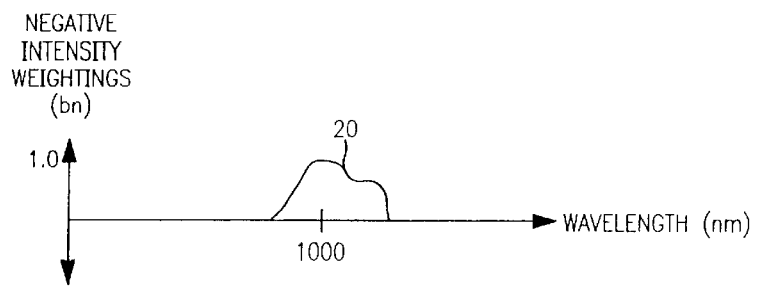
FIG. 3D is a graphical representation of the negative component of the spectroscopic regression vector as in FIG. 1.

FIG. 3A illustrates a single optical filter 52. Since the optical filter of this embodiment is a transmission filter which passes a certain percentage of incident light at each wavelength, it is unable to apply negative weightings. It is very unlikely, however, that the regression vector will be entirely positive. That is, it is unlikely that each regression constant $b_n$ will be positive. To account for positive and negative constants $b_n$ of an exemplary regression vector 20 as in FIG. 1, a system as illustrated in FIG. 3B includes a collimator 50 including a pair of collimating lenses 51$a$ and 51$b$ directing light to filter devices 52$a$ and 52$b$, respectively. Filter 52$a$ is weighted with the positive portion of the regression vector 20 (FIG. 1) as shown in FIG. 3C, and filter 52$b$ is weighted with the negative portion as illustrated as in FIG. 3D. A pair of detectors 56$a$ and 56$b$ receive the output light 54 from filter 52$a$ and 52$b$, respectively. Processor 58 sums the positive output from detector 56$a$ with the negative output from detector 56$b$ to provide the dot product of the regression vector and the light from sample 48. It should be understood that the output of detector 56$b$ is positive but that the output is summed to the detector 56$a$ output as a negative number. That is, processor 58 subtracts the output of detector 56$b$ from the output of detector 56$a$.

The regression vector constants $b_n$ are most likely between −1 and 1 and are likely to be relatively close to 0. Since, in the embodiment of optical filter 52 illustrated in FIGS. 3A and 3B, these numbers represent percentages of incident light passed to the detectors, the signal-to-noise ratio may be improved by unitizing the regression vector constants. That is, the constant $b_n$ having the largest absolute value is scaled to 1 or −1, depending on whether the constant is positive or negative. All the other constants $b_n$ are scaled by the same factor. These scaled constants then become the weightings $b_n$ by which filter 52 weights incident light at each wavelength. The output from the filter is then reduced by this scaling factor in the manner described above regarding the scaling factor caused by the use of normalized orthogonal components. That is, the regression vector'n unitization modifies the scaling factor resulting from regression vector normalization.

Although unlikely, it is possible that one or more of the constants $b_n$ of Equation 3 may be greater than 1 or less than −1. Although it is possible to use optical filter mechanisms, such as are described below, which are able to amplify light at different wavelengths, a scaling factor less than 1 may be used to reduce the constant $b_n$ so that the greatest magnitude constant is 1 or −1. The unitized constants may then be used by an optical filter such as filter 52 described above.

Figure 7A:
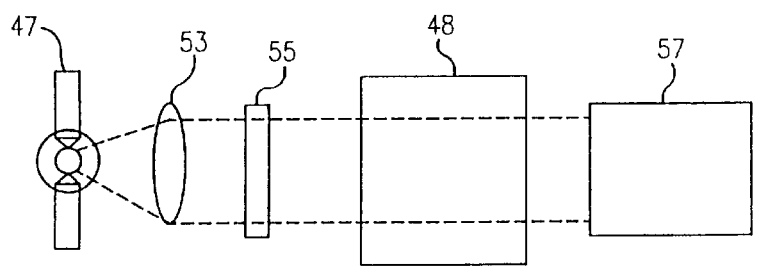
FIG. 7A is a schematic illustration of the present invention utilizing an absorption spectroscopy method.

Those of ordinary skill in this art should understand that energy source 46 may include various suitable energy sources, for example as are used in known spectroscopy methods. For example, referring to FIG. 7A, energy source 46 may include a broad band light source 47 proximate sample 48. Exemplary broad band light sources include lamps, filaments, LEDs, or other devices providing multi-wavelength light substantially over the visible and near visible light spectrum. One or more broad band sources may be positioned proximate sample 48 so that light emanating from the light source is directed by lens 53 to bandpass filter 55, which limits the light to a wavelength range equal to or within the regression vector wavelength range, and then on to the sample. This light may then pass through, as shown in FIG. 7A, or reflect from the sample to be analyzed downstream by optical system 57 to derive desired information about the sample. Optical system 57 includes an optical filter mechanism such as illustrated in FIG. 3B. Examples of such absorbance spectroscopy methods include infrared absorbance, near infrared absorbance(NIR), mid infrared absorbance(MIR) and ultraviolet visible absorbance(UV-VIS).

Energy source 46 may also illuminate sample 48 by exciting the sample so that it emits light. Such energy sources may include lasers, lamps or electricity sources. For example, referring to FIG. 7B, a laser or lamp 47 emits light that is filtered and directed to sample 48 by lenses 53a and 53b and bandpass filter 55. Sample 48 is excited so that it emits light, which is directed by lens 53c to system 57 for further analysis. Examples of such spectroscopy methods include fluorescence emission, phosphorescence emission, luminescence emission and electroluminescence.

Figure 7B:
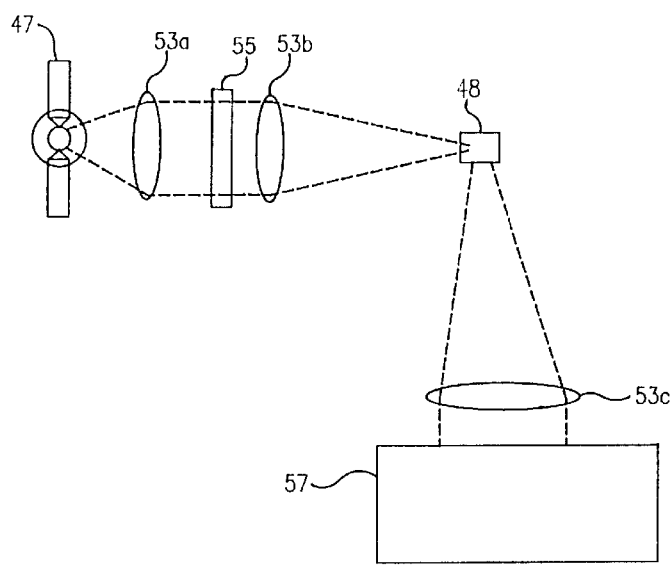
FIG. 7B is a schematic illustration of the present invention utilizing an emission or a scattering spectroscopy method.

FIG. 7B may also be used to illustrate scattering methods in which energy source 46, which typically includes a laser 47, exposes sample 48 to monochromatic light. As light passes through the sample, it is scattered into various wavelength bands. Examples of such methods include Raman scattering, Mie scattering, Rayleigh scattering and quasi-elastic light scattering. The configuration illustrated in FIG. 7B may be used in both emission methods and scattering methods, primarily because luminescence and scattering effects normally coexist, and the difference between these method types is largely a matter of analyzing the output. Certain circumstances, for example the wavelength of the energy used to illuminate the sample, or the sample itself, may cause one effect to dominate ever the other.

It should be understood that any of the above-described, or other suitable illumination methods may be employed with the present invention. Those of ordinary skill in this art should understand such methods and systems, and further detailed explanation thereof is therefore not provided.

Figure 7C:
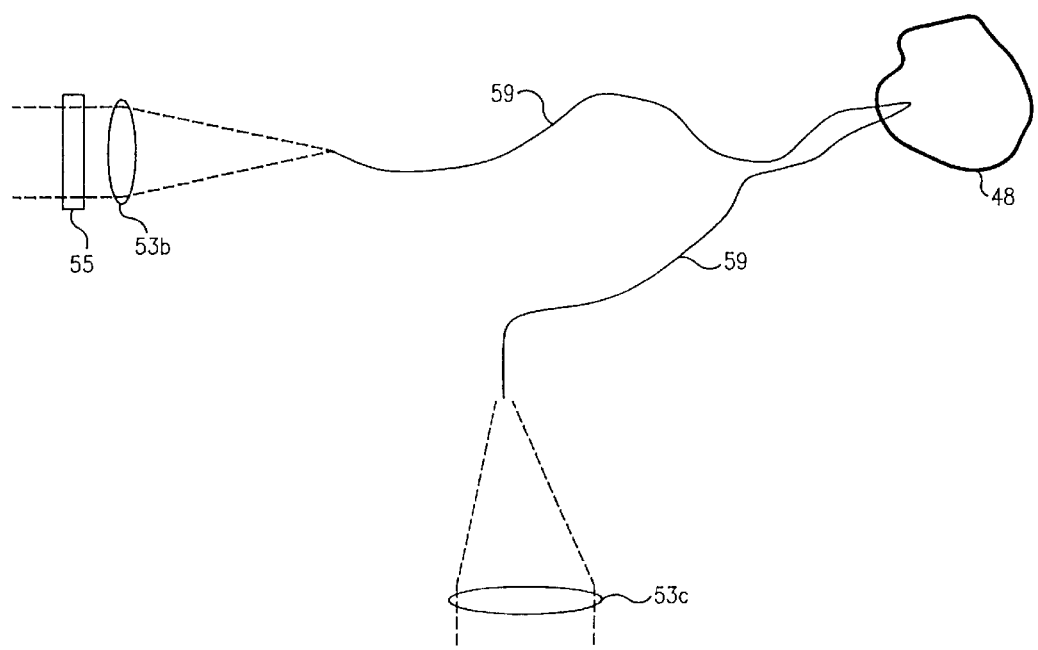
FIG. 7C is a partial schematic illustration of the present invention wherein light is directed to and from a sampled substance over optical fiber.

In the examples illustrated in FIGS. 7A and 7B, light is conveyed to and from sample 48 over air. It should be understood, however, that other light media may be used, for example fiber optic elements 59 as illustrated in FIG. 7C.

A spectroscopic regression vector is affected by the instruments and methods used to drive it. Thus, once a regression vector has been established with certain equipment, an equipment change may require a calibration of the system. To effect a calibration without recalculating the regression vector, filters may be placed between the filters 52a, 52b and detectors 56a, 56b shown in FIG. 3B. Alternatively, adjustable amplifiers may adjust the detector output, or processor 58 may be reprogrammed or recalibrated.

Calibration, and other system adjustments, may be easily effected where the system is configured to execute the regression vector equation as in Equation 2. A series of optical filter pairs, such as filters 52a and 52b in FIG. 3B, may be used to separate the orthogonal components from the light sample. Amplifiers may then apply the regression components $a_n$ as in Equation 2 to the output of the detectors following each optical filter pair. If the amplifiers are adjustable, the regression vector constants may be adjusted directly to account for the calibration. This type of arrangement may also be used where a product change requires redetermination of the regression vector. For example, a change in a refinery's manufacturing process or ambient conditions may change the regression vector. The adjustable amplifiers permit the change without requiring new optical filters. While the Equation 2 arrangement requires more filters than the Equation 3 arrangement, the expense may be justified if the regression vector is likely to change. A more detailed description of an Equation 2 arrangement is provided below.

It should also be understood that the shape and magnitude of the regression vector will depend upon the method used to derive it. For example, in terms of frequency, Raman spectroscopy produces sharp (for example, 10 cm$^{-1}$) peaks, while near infrared spectroscopy produces broader (for example 100 cm$^{-1}$) peaks, and UV-VIS spectroscopy produces very broad (for example, 500 cm$^{-1}$) peaks. Thus, the wavelength distribution is different for the different types of spectroscopy. Although the magnitudes may differ, all regression vectors may be scaled to unit weightings, for example through appropriate filter configuration. As noted above, subsequent electronics may provide correction via an amplifier or other suitable device. Although it may be possible to use different spectroscopy methods in deriving the regression vector and in performing the subsequent analysis if the filter is properly configured to account for the difference, it is preferred to use the same spectroscopy method for both.

Figure 8A:
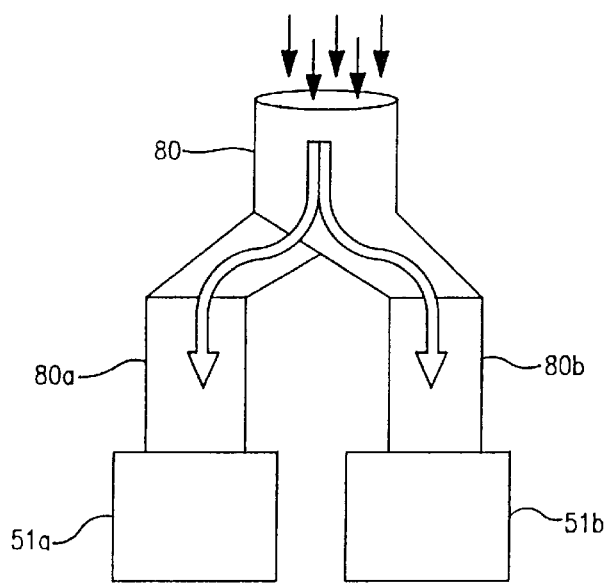
FIG. 8A is a schematic illustration of an optical fiber splitter mechanism for directing light from a sample to dual filters for separately weighting positive and negative regression vector portions.
Figure 8B:
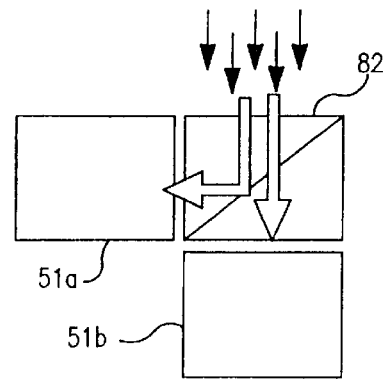
FIG. 8B is a schematic illustration of a beam splitter for directing light from a sample to dual filters for separately weighting positive and negative regression vector portions.

Light from sample 48 may be directed to lenses 51a and 51b by any of several suitable methods. Referring to FIG. 8A, for example, light may be conducted from the sample to the lenses 51a and 51b over fiber optic cable 80 constructed in a bundle branching into two sections. Light striking the combined face of the fiber bundle is separated into two divisions 80a and 80b which approach the lenses. Alternatively, referring to FIG. 8B, a beam splitter 82 may be used to separate the light, as should be understood by those of ordinary skill in this art. The beam splitter assembly could be neutral, splitting every wavelength nearly equally into two directions, or dichroic, sending some wavelengths in one direction and others in another. In another configuration, light is split by the disposition of the filters 52 rather than by an upstream device. Thus, a single lens collimator 50 is used to direct light from the sample to the filters.

Figure 8C:
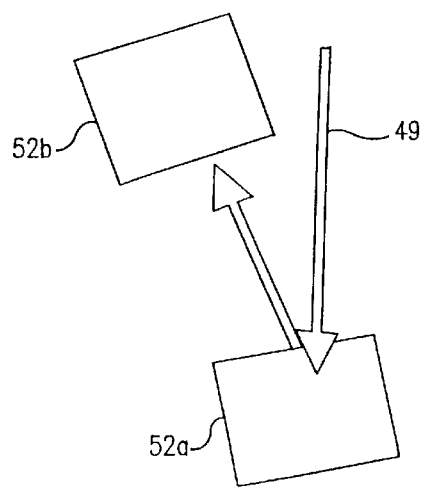
FIG. 8C is a schematic illustration of dual filters disposed to separately weight positive and negative regression vector portions.

The first of the filters, for example filter 52a in FIG. 8C, is disposed to operate at a slight angle, for example 10°, with respect to the path of light 49. Detector 56a (not shown in FIG. 8C) is disposed beyond filter 52a to receive the light transmitted by the filter. The light of all wavelengths not passed by filter 52a is reflected at an angle of 20° from the path of light 49. Filter 52b is disposed to operatively receive this light, and detector 56b (not shown in FIG. 8C) is disposed beyond filter 52b to receive the weighted light therefrom. Processor 58 (not shown in FIG. 8C) measures the output of the two detectors as described above. Since filters 52a and 52b never have overlapping transmission, the reflected light from the first can feed the second filter directly, obviating the need to separate the light prior to filtering.

Figure 6:
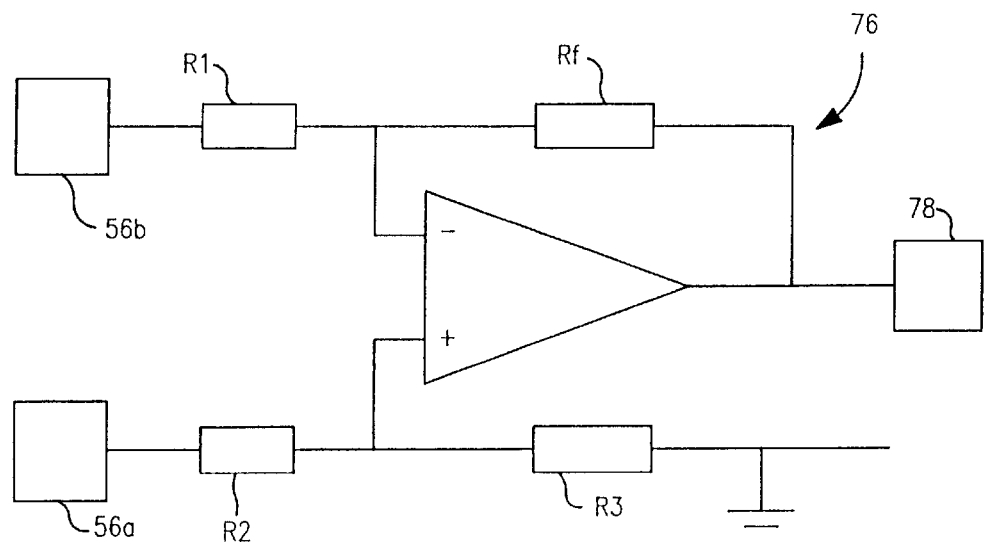
FIG. 6 is a schematic illustration of a summing circuit for summing weighted positive and negative light component portions.

One exemplary embodiment of processor 58 is schematically illustrated in FIG. 6. Output signals from detector 56a and 56b are provided to a resistor and op-amp circuit 76. Since the outputs from the detectors are positive, the summing circuit performs a subtraction function. Specifically, the output to display device 78 is given by the equation $$v_O = (R3/R1)((R1+Rf)/(R2+R3))56a - (Rf/R1)56b.$$

By appropriately selecting the resistor values, the amplifier gains, if different, can be compensated and the correct substraction performed.

Various suitable filter mechanisms other than the filter devices described above with respect to FIG. 3B may be used for optical data compression. Although the discussion below provides examples of such mechanisms in the context of an Equation 3-type regression vector arrangement, it should be understood that such mechanisms may be applied in other embodiments described herein.

Figure 4A:
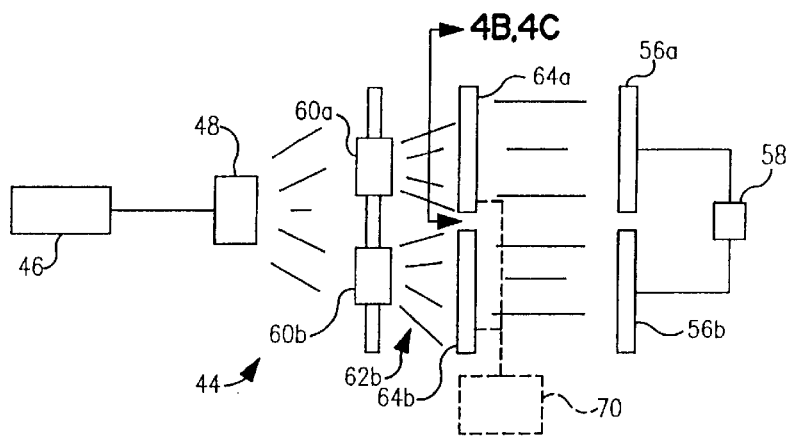
FIG. 4A is a schematic illustration of an optical analysis system according to the present invention.

Accordingly, in the embodiment illustrated in FIG. 4A, an optical filter mechanism includes a pair of spectrographs 60a and 60b and a pair of optical filters 64a and 64b. Light from sample 48 is directed to spectrographs 60a and 60b, which output light spectra 62a and 62b to the filters. The operation and construction of a spectrograph should be well known to those of ordinary skill in this art and are, therefore, not described in detail herein. In general, however, each spectrograph includes a narrow input slit of a given height and produces an output spectrum much broader than the input slit but having the same height. The light intensity varies laterally across the spectrum by light wavelength.

Figure 4B:
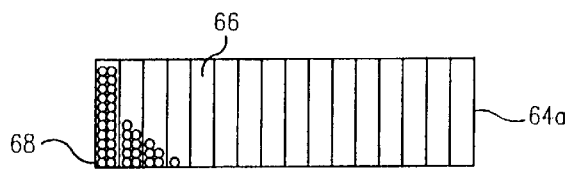
FIG. 4B is a schematic illustration of an exemplary filter device for use in the system as in FIG. 4A.

As discussed above regarding the system illustrated in FIG. 3B, the system of FIG. 4A separately weights the positive and negative regression vector constants. Thus, the system includes two filters 64a and 64b, weighted with the positive and negative constants, respectively. Although configured to the different weightings, the structure and general operation of the two filters is the same. Accordingly, only filter 64a is illustrated in FIG. 4B. Referring to FIG. 4B, filter device 64a includes a plurality of areas 66 arranged so that each area 66 receives light of a particular wavelength in spectrum 62a. Since areas 66 have a certain width, each receives light from spectrum 62a over a certain wavelength range. However, the range is small and may be considered a single wavelength as used herein.

The total spectrum wavelength range depends, for example, on the spectroscopy method used. For example, Raman typically covers a more narrow range than NIR. Also, some sections of the optical spectrum may contain more information than other sections. Thus, some spectrum sections may be omitted from the regression vector to improve performance.

Filter device 64a weights the intensity of light at each wavelength in spectrum 62a as determined by the spectroscopic regression vector. The weightings may be effected in various suitable fashions. For example, each area 66 may include a plurality of light sensor devices 68, for example including liquid crystal display devices (LCDs) or fiber optic elements. Each device 68 detects the presence or absence of incident light. Thus, the weighting at any given area 66 may be determined by selecting the number of devices 68 which will be measured. For example, a certain number of devices 68 may be deactivated, or a control system may selectively monitor the output of a predetermined number of the devices. Weighting may also be accomplished by selecting the density of the sensor devices 68 over the various wavelengths. Again, the weightings at a given "wavelength" will be applied over a certain range. For example, since fiber optic elements are approximately 0.3 nm wide in wavelength space, the wavelength range of a particular area is approximately 0.3 nm.

Filter 64a and an associated control system may comprise a single unit which weights light from spectrograph 60 and detects the weighted light. Such a control system may include a computer device 70 for controlling the operation of the filters and monitoring their output.

Figure 4C:
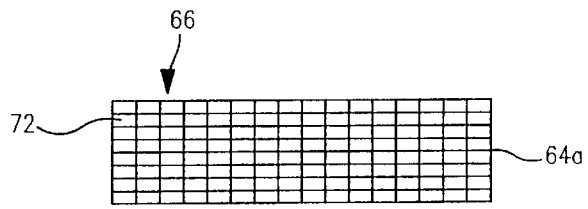
FIG. 4C is a schematic illustration of an exemplary filter device for use in the system as in FIG. 4A.

In another preferred embodiment, filter devices 64a and 64b may each include an array of transmission filters configured to selectively pass light to detector devices 56a and 56b, respectively. Referring to FIG. 4C, each area 66 of filter 64a includes a plurality of transmission filters 72 so that the amount of light measured by detector 56a at each wavelength along the spectrum 62a is determined by the number of transmission filters which pass light at each area 66. The number of transmission filters passing light at each area is determined by the weightings of the regression vector. The filters 72 may include, for example, adjustable shutters which may be selectively opened or closed. Thus, the number of open or closed shutters in a given area 66 determines the percentage of light passed from that area to the detector 56a.

Alternatively, filters 72 may be constructed so that each passes a predetermined percentage of incident light, thereby causing the area 66 to pass a predetermined percentage. By including the proper such filters, which may include, for example, photographic film plates or holographic optical elements, the light passing percentages at each area 66 may be set to the regression vector weighting at the relevant wavelength.

Filters 64a in FIGS. 4B and 4C may be adjustable so that the weightings at each wavelength may be changed to accommodate a new regression vector. For example, a number of sensors 68 may be selectively activated, deactivated or monitored as needed, for example by computer device 70. Similarly, transmission filters 72 may be activated, deactivated or otherwise configured, for example manually or by computer 70, to pass or reject light as needed.

Figure 5:
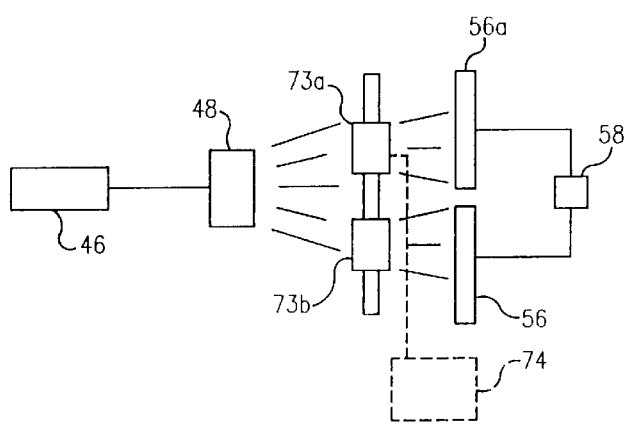
FIG. 5 is a schematic illustration of an optical analysis system according to the present invention.

In another preferred embodiment illustrated in FIG. 5, light from sample 48 is weighted by acoustooptical filters 73a and 73b. Again, two filters are used to accommodate positive and negative regression vector constants. Each filter 73a and 73b passes light at a single wavelength at a time, the wavelength being determined by acoustic wave control signals from computer 74. The filters weight the light from sample 48 by varying the time over which light is passed at each wavelength. By setting the relative time periods at each wavelength to correspond to the relative weightings at each wavelength in the regression vector, the filters weight the light in a pattern that corresponds to the regression vector. Light detector devices 56a and 56b measure the intensity of light passed from filters 73a and 73b as they scan through the applicable wavelength range. Processor 58 sums the positive component from detector 56a with the negative component of detector 56b. Alternatively, filters 73a and 73b may be liquid crystal tunable filters. The operation of crystal tunable filters, as should be understood by those of ordinary skill in this art, is similar to that of acoustooptical filters.

While the acoustooptical filters are described above as passing light at a particular wavelength, it should be understood that light is passed over a relatively small wavelength range. For example, an acoustooptical filter may have a bandwidth near 10 nm. As discussed herein, however, these ranges may be considered single wavelengths for a given application.

While the embodiments of the present invention discussed above weight the intensity or, similarly, time of light intensity exposure of light from the sample substance, it should be understood that other properties of light may be weighted. For example, light polarization or coherence may be weighted as a function of wavelength.

The present invention may be used to optically compress light data in applications in which the regression vector constants may change from sample to sample and in applications not suitable for principal component analysis. For example, a class of substances may produce the same principal components but not be subject to a unique regression vector. Gasolines again provide an example. All gasolines are composed of the same major compounds, but a high octane gasoline may be obtained in various ways by mixing different compounds. Particularly, mixtures may vary from manufacturer to manufacturer. Principal component analysis performed on sample gasoline spectra from different manufacturers may reveal that the gasolines have the same, or very similar, principal components but that the relative importance of the components differs among the manufacturers. Consequently, the regression vector of the gasoline of one manufacturer will be different from that of another. Another example is the prediction of blood glucose levels using light transmitted through blood samples. A regression vector may be determined for an individual to relate the blood principal components to blood glucose level. From this point on, this person's blood glucose level may be monitored optically. If the same instrument is used on another person, however, the glucose measurement may fail, even though the principal components for the two individuals are the same. Differences between the individuals, for example race, blood type, or weight, may cause the weightings of the principal components to differ so significantly that the regression vector for the first individual is not applicable to the second.

Figure 9:
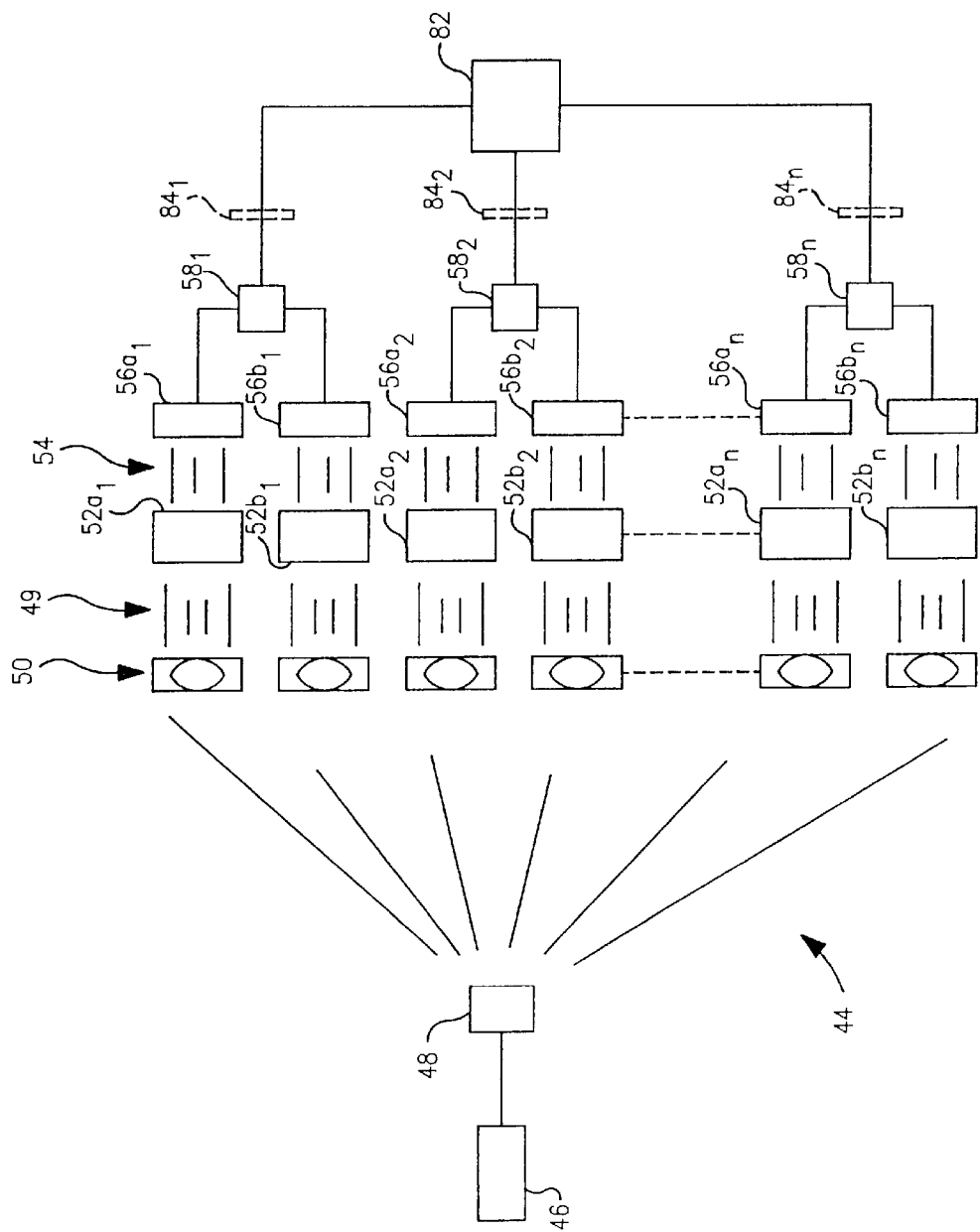
FIG. 9 is a schematic illustration of an optical analysis system according to the present invention.

An optical analysis system 44 illustrated in FIG. 9 may be effectively used in these situations to optically compress light data from non-similar light sources to derive desired information. An energy source 46 illuminates a sample, for example a blood sample, 48 by any suitable method as described above. Light from illuminated sample 48 is conveyed by suitable means to a series of collimators 50 which direct the light in parallel beams 49 to a series of optical filter devices. The optical filters may be constructed, for example, as the optical filters 52a and 52b discussed above regarding FIG. 3B. The optical filters are grouped in pairs, each pair corresponding to a principal component applicable to the sample, in this case human blood. Thus, optical filters $52a_1$ and $52b_1$ may correspond to the positive and negative portions, respectively, of the first principal component. Optical filters $52a_2$ and $52b_2$ correspond to the second principal component. Additional filter pairs follow up to filters $52a_n$ and $52b_n$, where n is the number of principal components.

The arrangement as in FIG. 9 may be used to derive information from a light sample using the regression vector format as in Equation 2. Since a regression vector for one sample is inapplicable to other samples, there are no regression constants a through $a_n$ that can be used for each blood sample. Thus, in constructing the optical filters, these constants are assumed to be 1. The optical filter weighting percentages, therefore, correspond to the values of the normalized principal components at each wavelength. For example, the normalized first principal component may have a value of −0.04 at 500 nm. Thus, the weighting percentage of optical filter $52b_1$ at 500 nm is 4%, and the weighting of optical filter $52a_1$ at the same wavelength is 0. The components may also be unitized to improve the signal-to-noise ratio. Accordingly, each optical filter pair performs the dot product of the light from the light source with its respective principal component vector, and the amount of light output from the optical filter pair is proportional to the contribution of that principal component to the original light from the sample. Again, the proportionality is due to the normalization and unitization of the component vector. This may be accounted for by processor 58, which sums the output of the light detectors 56a and 56b or by a downstream computing device 82.

The optical filter mechanism of FIG. 9 compresses the data carried by the light from the light source into principal components in a manner so that the principal component magnitudes may be separately detected. Accordingly, a display device such as an LED (not shown) may be attached to the output of each processor 58. Assuming that the proportionality for each component is accounted for in some manner prior to the processor output, such devices display the magnitude of each component in the original light.

This system may be used to accurately measure the blood glucose level of any individual. For example, several blood samples may be drawn from an individual and analyzed by the system to determine the magnitude of each principal component in each sample. This data may be directed to a computer 82, or other suitable device, which performs a multiple linear regression of the component magnitudes for each sample against the blood glucose level for each sample measured by conventional means. The regression produces the regression constants $a_0$ through $a_n$ of Equation 2. The constants may be applied to the output from subsequent blood samples by computer 82 so that the system may be used to accurately measure blood glucose for this individual.

In another embodiment, computer 82 is not used in measuring subsequent blood samples. Instead, a series of adjustable amplifiers 84 apply a gain to the detector outputs equal to the respective regression constants $a_1$ through $a_n$. A summing circuit, which may include any suitable mechanism such as a microprocessor or summing circuitry, may be used to sum the output of each amplifier 84. The output of the summing device may then be offset by the constant $a_0$ and scaled by a scaling factor as described above by an appropriate amplifier or computing device. The offset mechanism may be any suitable device which, for example, adds or subtracts an appropriate DC offset to or from the detector output. The offset mechanism and the scaling factor amplifier may also be adjustable.

Accordingly, the system as in FIG. 9 may be used to analyze any sample having the principal components embodied by the optical filters. It may be used to determine the regression vector constants for similar samples and thereafter, by appropriately setting the adjustable gains and offset, to apply the appropriate regression vector for those samples. Such a system may also be used where a regression vector is known to change over time. Thus, rather than constructing a single optical filter pair to perform the dot product according to the Equation 3 regression vector, a refinery may use an adjustable configuration as shown in FIG. 9 so that the regression vector may be changed as needed.

It should also be understood that the system illustrated in FIG. 9 may be constructed in various suitable forms. For example, various suitable combinations of computing devices and/or amplifiers and/or optical filters may be used to effect the gains, offsets and summations applied and performed by the system. For example, the detector outputs may all be directed to a computer which may perform all of these functions. Furthermore, the system may be packaged in a relatively small kit with an energy source capable of illuminating a blood sample so that, once the appropriate gains and offset are set, an individual may perform glucose testing at home. Principal components are merely one set of orthogonal components. They are very useful in that they represent the most compact form of data compression. That is, they represent the fewest number of orthogonal components that completely describe the data in the original signal. If light is to be analyzed from sources having different principal components, however, principal component analysis is not an effective data compression tool. Thus, it should be understood that the filter mechanism of the present invention may compress light data into orthogonal components other than principal components, for example Fourier components or wavelet components. Like principal components, these other component types are orthogonal components of the original waveform. They are not, however, as efficient as principal components, and more components are necessary to adequately describe the light data. For example, each Fourier component has the shape of a sine wave. Thus, the Fourier components are a series of sine waves of different magnitudes and frequencies which, when combined, produce the original signal. Each sine shape may be normalized and/or unitized so that each component may be used as weightings for an optical filter pair such as filters $52a_1$ and $52b_1$ in FIG. 9. Thus, the system in FIG. 9 could be configured to compress the light data into Fourier components.

Embodiments of the present invention using non-principal component data compression may be used in a variety of applications. For example, the present invention may be used with satellite systems that receive light reflected from the earth and relay light data to the earth for analysis to derive desired information, for example the location of oil deposits. In this case, the light source is light reflected from earth rather than light from an illuminated sample substance. Light reflected from different parts of the earth may have very different principal components, but may still be affected by oil deposits beneath the surface. A series of optical filters may be constructed to compress the data carried by this light into a predetermined set of orthogonal components, for example Fourier or wavelength components. An optical filter pair, such as illustrated in FIG. 9, may be constructed for each component and housed in the satellite. The earth's surface may be imaged through each filter pair in turn to provide a compact data set containing all the pertinent spectroscopic data that can be obtained. Thus, the satellite carries an optical filter for each significant component and, for example, a separate camera for each optical filter or one camera that sequentially views the earth's surface through each filter. This compact information may be transmitted to a processing unit on earth, where the spectra can be reconstituted from the compact representation of Fourier or wavelet components. The number of components used may be chosen to provide a desired spectroscopic resolution. That is, the more components used, the more accurately the actual spectrum may be recreated. Thus, earth-based researchers may have at their disposal all the significant optical information about the earth's surface.

The present invention may also be used in systems such as communication systems where information is stored in predetermined orthogonal components. Light comprising the components is transmitted through an optical medium to a set of filters configured to compress the light to the components to derive the information. By using orthogonal components, multiple signals may be transmitted simultaneously without interference.

Such a system is particularly advantageous in long range optical communications systems that transmit information in wavelenth-division multiplexing (WDM).

In current communications systems, the use of WDM is limited by overlap of neighboring wavelength channels. For example, if the closest spacing of WDM channels without overlap is 10 nm, and if the wavelength band is approximately 100 nm, at most 10 channels may be simultaneously transmitted. Using the present invention, a far greater number of channels may be arranged as orthogonal components in wavelength space and combined to be simultaneously transmitted over an optical medium, at the end of which a group of optical filters compresses the data into the orthogonal components for measurement. Channel overlap does not damage data transmission integrity because the channels are orthogonal to one another.

In one preferred embodiment, each channel takes the form of some predefined signal, for example a pulse having some shape. The pulses are orthogonal to each other. To create orthogonal pulses, each pulse is configured so that if each is plotted as a function of wavelength, the dot product of any pulse with any other is zero. Any number of these pulses may be transmitted over the optical medium, for example fiber optic cable, to a series of optical filters. Thus, one or more optical transmission line is the light source for the optical filters. Each optical filter pair in the series may be configured as described above so that it performs the dot product of the light from the fiber optic cable with a particular one of the orthogonal shapes. Thus, the optical filter series compresses the light data into predefined transmission channel components.

Each orthogonal shape may be normalized and/or unitized so that an optical filter such as described above regarding FIGS. 3 and 9 may be used. If a pulse corresponding to any particular filter pair is not present in the light signal, the output from the detectors corresponding to this filter pair is zero. If a pulse is present, the detectors measure a value dependent upon the magnitude of the pulse in the signal. Since this magnitude may be predetermined, the system may be configured to look for a particular level to identify the presence of a pulse. In this way, a far greater number of pulses may be conveyed and recognized over optical media than is possible in conventional systems.

The limit to the number of orthogonal signals may be determined by the modulation frequency of the channel. For example, a 10 GHz data rate on one channel blurs its spectrum by 10 GHz. If Fourier functions are used, the spacing between crests of the most complex filter will not be closer than 10 GHz. This represents the maximum theoretical data transmission rate—approximately 10 to 100 times greater than conventional WDM systems. The Fourier functions may be constructed from etalons, which have sine wave spectra. An etalon is analogous to a pair of mirrors with a spacer between them. Different spacer thicknesses provide different sine functions. An orthogonal system may use WDM channels by transmitting orthogonal functions inside each WDM channel.

As indicated above, the present invention may be utilized in a variety of environments. For example, the process of reading gel electrophoresis plates in conventional genetics testing is relatively time and labor intensive. Using the present invention, light passed through a photograph of a gel electrophoresis plate may be directed to optical filters which compress the light data into orthogonal components corresponding to particular taggants.

While preferred embodiments of the invention have been described above, it should be understood that any and all equivalent realizations of the present invention are included within the scope and spirit thereof. Thus, the embodiments depicted are presented by way of example only and are not intended as limitations upon the present invention. Therefore, it is contemplated that any and all such embodiments are included in the present invention as may fall within the literal or equivalent scope of the appended claims.

What is claimed is:

1. An optical analysis system, said system comprising:
   an optical filter mechanism disposed to receive light from a light source and configured to optically filter a plurality of orthogonal components of said light therefrom, wherein each said orthogonal component has a predetermined shape, with respect to a property of said light, that varies over a predetermined wavelength range; and
   a detector mechanism in operative communication with said optical filter mechanism to measure a property of said light filtered by said optical filter mechanism,
   wherein said optical filter mechanism is configured so that the magnitude of said property measured by said detector mechanism is proportional in a predetermined relationship to desired information carried by said light.

2. The system as in claim 1, including a said light source.

3. The system as in claim 2, wherein said light source includes an energy source configured to illuminate a substance.

4. The system as in claim 3, wherein said energy source includes a broad band light source disposed relative to said substance so that said broad band light source exposes said substance to broad band light.

5. The system as in claim 3, wherein said energy source is configured to excite said substance so that said substance emits light.

6. The system as in claim 3, wherein said energy source includes a monochromatic light source disposed relative to said substance so that said monochromatic light source exposes said substance to monochromatic light so that said monochromatic light is scattered by said substance into a plurality of wavelengths.

7. The system as in claim 1, including at least one collimator disposed relative to said light source and said optical filter mechanism to collimate and direct said light from said light source to said optical filter mechanism.

8. The system as in claim 1, wherein said optical filter mechanism includes a plurality of optical filter devices, each said optical filter device filtering one of said orthogonal components from said light.

9. An optical analysis system, said system comprising:
   an optical filter mechanism disposed to receive light from a light source and configured to optically filter data carried by said light into at least one orthogonal component of said light;
   a detector mechanism in operative communication with said optical filter mechanism to measure a property of said at least one orthogonal component to measure said data; and
   a gain mechanism in operative communication with at least one of said optical filter mechanism and said detector mechanism and configured to weight said property of each said at least one orthogonal component.

10. The system as in claim 9, wherein said gain mechanism is adjustable so that the weighting applied to each said at least one orthogonal component by said gain mechanism is selectable.

11. The system as in claim 9, wherein said gain mechanism is configured to weight said each at least one orthogonal component according to the amount of data it carries relating to desired information about said light source.

12. The system as in claim 9, wherein said gain mechanism includes an optical filter device configured to weight said property of light received by said optical filter device by a predetermined weighting.

13. The system as in claim 9, wherein said detector mechanism produces an electrical signal corresponding to said measured property and wherein said gain mechanism includes an electrical gain device configured to weight said output signal.

14. The system as in claim 9, wherein said gain mechanism is disposed upstream from said optical filter mechanism.

15. The system as in claim 9, wherein said gain mechanism is disposed downstream from said optical filter mechanism.

16. The system as in claim 9, wherein said gain mechanism and said optical filter mechanism are of a unitary construction.

17. The system as in claim 9, wherein said gain mechanism and said detector mechanism are of a unitary construction.

18. The system as in claim 1, wherein said optical filter mechanism is configured to weight the intensity of said light from said light source to perform the dot product of said light and each said orthogonal component by wavelength and wherein said detector mechanism measures the intensity of said weighted light.

19. The system as in claim 8, wherein each said filter device is configured to weight the intensity of said light from said light source to perform the dot product of said light and the said orthogonal component filtered by said filter device by wavelength and wherein said detector mechanism measures the intensity of said weighted light.

20. The system as in claim 8, wherein said optical filter mechanism filters said data carried by said light into principal components and wherein each said optical filter device filters one said principal component from said light.

21. The system as in claim 8, wherein said optical filter mechanism filters said data carried by said light into Fourier components and wherein each said optical filter device filters one said Fourier component from said light.

22. The system as in claim 8, wherein said optical filter mechanism filters said data carried by said light into wavelet components and wherein each said optical filter device filters one said wavelet component from said light.

23. An optical analysis system, said system comprising:
   an optical filter mechanism disposed to receive light from a light source and configured to optically filter data carried by said light into principal components of said light; and
   a detector mechanism in operative communication with said optical filter mechanism to measure a property of said principal components to measure said data.

24. The system as in claim 1, wherein said orthogonal components are Fourier components.

25. The system as in claim 1, wherein said orthogonal components are wavelet components.

26. The system as in claim 1, wherein said optical filter mechanism includes a single optical filter device configured to filter said plurality of said orthogonal components.

27. The system as in claim 26, wherein said orthogonal components are principal components.

28. The system as in claim 26, wherein said single filter device weights said orthogonal components according to a regression vector related to desired information about said light source.

29. An optical analysis system, said system comprising:
an optical filter mechanism disposed to receive light from a light source and configured to optically filter data carried by said light into at least one orthogonal component of said light;
a detector mechanism in operative communication with said optical filter mechanism to measure a property of said at least one orthogonal component to measure said data; and
a spectrograph device disposed relative to said light source and said filter mechanism so that said spectrograph device directs light from said light source to said filter mechanism, said spectrograph device separating said light into a spetrum.

30. The system as in claim 29, wherein said optical filter mechanism includes at least one optical filter device having predetermined areas arranged so that each said area receives light of a predetermined wavelength from said light spectrum and wherein each said area filters from said predetermined wavelength light the part of at least one said orthogonal component present at said predetermined wavelength.

31. The system as in claim 29, wherein said at least one optical filter device includes a holographic filter configured to selectively pass predetermined amounts of light at each said predetermined area.

32. The system as in claim 30, wherein said at least one optical filter device includes an array of light sensor devices, wherein each said predetermined area includes a plurality of said light sensor devices configured to detect the presence or absence of light incident thereon, and wherein the amount of light detected at each said predetermined area is determined by selecting the number of said sensor devices measured by said detector device.

33. The system as in claim 32, wherein said light sensor devices include liquid crystal display devices.

34. The system as in claim 32, wherein said light sensor devices include fiber optic elements.

35. The system as in claim 30, wherein said at least one optical filter device includes an array of transmission filters, each said transmission filter configured to selectively pass light to said detector mechanism and wherein each said predetermined area includes a plurality of said transmission filters so that the amount of light measured by said detector device at each said wavelength is determined by the number of said transmission filters which pass light at each said predetermined area.

36. The system as in claim 35, wherein said transmission filters comprise shutters.

37. The system as in claim 35, wherein said transmission filters comprise photographic plates.

38. The system as in claim 35, wherein said transmission filters comprise holographic optical elements.

39. An optical analysis system, said system comprising:
an optical filter mechanism disposed to receive light from a light source and configured to optically filter data carried by said light into at least one orthogonal component of said light; and
a detector mechanism in operative communication with said optical filter mechanism to measure a property of said at least one orthogonal component to measure said data,
wherein said optical filter mechanism includes at least one optical filter device configured to receive light from said light source and to pass said light to said detector mechanism, said optical filter device varying the duration of passage of said light to said detector mechanism by wavelength according to the proportion of light at each wavelength contributed by one or more said orthogonal components.

40. The system as in claim 39, wherein said at least one optical filter device includes an acoustooptical filter.

41. The system as in claim 39, wherein said at least one optical filter device includes a liquid crystal tunable filter.

42. The system as in claim 19, wherein said optical filter mechanism includes at least one said optical filter device configured to separately weight said light from said light source into a positive portion of its said one orthogonal component and a negative portion of its said one orthogonal component, and wherein one of said optical filter mechanism and said detector mechanism sums the output of said positive component filtering and said negative component filtering.

43. The system as in claim 1, wherein said detector mechanism includes at least one detector device to measure said property and at least one output device in operative communication with said at least one detector device to output data corresponding to said measurement of said property.

44. The system as in claim 43, wherein said output device includes a general purpose computer.

45. The system as in claim 43, wherein said output device includes a display device to display said data corresponding to said measurement of said property.

46. The system as in claim 43, wherein said optical filter mechanism includes a plurality of optical filter devices, each said optical filter device filtering one of said orthogonal components from said light, wherein said detector mechanism includes a plurality of said detector devices, each said detector device measuring said property of a said orthogonal component filtered by one of said optical filter devices, and wherein said output device sums said measurements by said plurality of optical filter devices.

47. An optical analysis system, said system comprising:
an optical filter means for receiving light from a light source and optically filter a plurality of orthogonal components of said light therefrom, wherein each said orthogonal component has a predetermined shape, with respect to a property of said light, that varies over a predetermined wavelength range; and
a detector means for measuring a property of said light filtered by said optical filter means,
wherein said optical filter means is configured so that the magnitude of said property measured by said detector means is proportional in a predetermined relationship to desired information carried by said light.

48. An optical analysis system, said system comprising:
a light source;
an optical filter mechanism having a plurality of optical filter devices disposed relative to said light source to receive light therefrom, each said optical filter device being configured to filter from said light a respective orthogonal component of a plurality of predetermined orthogonal components of said light, wherein each said orthogonal component has a predetermined shape, with respect to a property of said light, that varies over a predetermined wavelength range;
a detector mechanism in operative communication with said optical filter mechanism to measure said property of said light filtered by said optical filter devices; and a gain mechanism in operative communication with at least one of said optical filter mechanism and said detector mechanism and configured to weight the magnitude of said property of said light filtered by at least one of said optical filter devices.

49. The system as in claim 48, wherein each said optical filter device is configured to weight the intensity of said light from said light source to perform the dot product of said light and one of said orthogonal components and wherein said gain mechanism is configured to weight said intensity of said weighted light.

50. The system as in claim 49, wherein said detector mechanism includes a plurality of detector devices, each said detector device disposed relative to a respective said optical filter device to measure the intensity of said weighted light therefrom, wherein each said detector device produces an electrical signal corresponding to said intensity of said weighted light and wherein said gain mechanism is configured to weight said electrical signals from said plurality of detectors.

51. The system as in claim 49, wherein said gain mechanism is adjustable so that the weighting applied to the intensity of the weighted light from each said optical filter device is selectable.

52. The system as in claim 49, wherein each said optical filter device includes a first portion to weight said light from said light source according to a positive portion of said orthogonal component and a second portion to weight said light according to a negative portion of said orthogonal component, and wherein one of said optical filter device and said detector device sums the output of said positive portion and said negative portion.

53. An optical analysis system, said system comprising:
a light source;
an optical filter device disposed relative to said light source to receive light therefrom and configured to weight the intensity of said light from said light source by wavelength according to a regression vector, said regression vector corresponding to the combination of a plurality of weighted orthogonal components of said light, wherein each said orthogonal component is weighted according to the amount of data it carries related to desired information about said light source and wherein said orthogonal components comprise a compression of data carried by said light; and
a detector device disposed relative to said optical filter device to measure the intensity of said weighted light therefrom.

54. The system as in claim 53, wherein said optical filter device includes a first portion to weight said light from said light source according to a positive portion of said regression vector and a second portion to weight said light according to a negative portion of said regression vector, and wherein one of said optical filter device and said detector device sums the output of said positive portion and said negative portion.

55. The system as in claim 48, wherein said gain mechanism is configured so that the magnitude of said property measured by said detector mechanism is proportional in a predetermined relationship to desired information carried by said light.

56. The system as in claim 48, wherein said optical filter mechanism and said gain mechanism are comprised of a plurality of tunable acoustooptical filters.

57. A method of determining information carried by light, said method comprising:
determining a plurality of orthogonal components of said light, wherein each said component has a predetermined shape, with respect to a property of said light, that varies over a predetermined wavelength range;
determining respective weightings for said orthogonal components so that the magnitude of said orthogonal components in a sample of said light, weighted by said weightings, is proportional to said information present in said sample in a predetermined relationship;
providing an optical filter mechanism configured to optically filter said orthogonal components;
disposing said optical filter mechanism to receive a sample of said light; and
detecting said property of said light sample filtered by said optical filter mechanism.

* * * * *

UNITED STATES PATENT AND TRADEMARK OFFICE
CERTIFICATE OF CORRECTION

PATENT NO. : 6,198,531 B1                                          Page 1 of 1
APPLICATION NO. : 08/891577
DATED : March 6, 2001
INVENTOR(S) : Michael L. Myrick, Matthew P. Nelson and Karl S. Booksh It is certified that error appears in the above-identified patent and that said Letters Patent is hereby corrected as shown below:

Column 1, line 2 following the Title of the Invention add:

--This invention was made with Government support under Grant No. CHE9403179 awarded by the National Science Foundation and Government support awarded by the Army Research Office under DAAH04-93-G-0324. The Government has certain rights to this invention.--

Signed and Sealed this

Fourteenth Day of December, 2010

David J. Kappos
*Director of the United States Patent and Trademark Office*